(12) United States Patent
Yokoyama et al.

(10) Patent No.: US 8,859,700 B2
(45) Date of Patent: Oct. 14, 2014

(54) METHOD FOR PRODUCING A WATER-ABSORBENT RESIN

(75) Inventors: Hideki Yokoyama, Himeji (JP); Sachi Kikuno, Kurobe (JP); Atsushi Heguri, Himeji (JP); Nobuhiro Maeda, Himeji (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 0 days.

(21) Appl. No.: 13/812,695

(22) PCT Filed: Jul. 20, 2011

(86) PCT No.: PCT/JP2011/066454
§ 371 (c)(1),
(2), (4) Date: Jan. 28, 2013

(87) PCT Pub. No.: WO2012/014748
PCT Pub. Date: Feb. 2, 2012

(65) Prior Publication Data
US 2013/0123455 A1    May 16, 2013

(30) Foreign Application Priority Data

Jul. 28, 2010    (JP) ................................ 2010-169677

(51) Int. Cl.

| | | |
|---|---|---|
| *C08F 2/20* | (2006.01) | |
| *C08F 2/32* | (2006.01) | |
| *A61L 15/24* | (2006.01) | |
| *C08F 2/18* | (2006.01) | |
| *C08F 2/00* | (2006.01) | |
| *C08F 220/06* | (2006.01) | |
| *A61L 15/60* | (2006.01) | |
| *C08F 2/10* | (2006.01) | |
| *C08F 2/24* | (2006.01) | |
| *C08F 4/04* | (2006.01) | |
| *C08L 33/08* | (2006.01) | |

(52) U.S. Cl.
CPC . *C08F 2/10* (2013.01); *A61L 15/24* (2013.01); *C08F 2/18* (2013.01); *C08F 2/001* (2013.01); *C08F 2/32* (2013.01); *C08F 2/24* (2013.01); *C08F 220/06* (2013.01); *C08F 2/20* (2013.01); *A61L 15/60* (2013.01); *C08F 4/04* (2013.01); *C08L 33/08* (2013.01); *Y10S 526/91* (2013.01); *Y10S 526/911* (2013.01)
USPC .................... 526/317.1; 526/910; 526/911

(58) Field of Classification Search
CPC ............. C08F 2/001; C08F 2/32; C08F 2/18; C08F 2/20; C08F 2/10; C08F 2/24; C08F 220/06; C08F 4/04; C08L 33/08; A61L 15/24; A61L 15/60
USPC ...................... 526/317.1, 910, 911
See application file for complete search history.

(56) References Cited

U.S. PATENT DOCUMENTS

| | | | |
|---|---|---|---|
| 5,652,309 | A | 7/1997 | Itoh et al. |
| 2007/0015887 | A1 | 1/2007 | Yoshino et al. |
| 2009/0036855 | A1 | 2/2009 | Wada et al. |
| 2009/0169891 | A1 * | 7/2009 | Higashimoto et al. ........ 428/402 |
| 2009/0182092 | A1 | 7/2009 | Yokoyama et al. |
| 2009/0281247 | A1 | 11/2009 | Handa et al. |
| 2010/0331802 | A1 * | 12/2010 | Yokoyama et al. ........... 604/372 |

FOREIGN PATENT DOCUMENTS

| | | | |
|---|---|---|---|
| CN | 1492884 | A | 4/2004 |
| EP | 2 184 300 | A1 | 5/2010 |
| JP | 61-087702 | A | 5/1986 |
| JP | 62-172006 | A | 7/1987 |
| JP | 03-195709 | A | 8/1991 |
| JP | 03-195713 | A | 8/1991 |
| JP | 09-012613 | A | 1/1997 |
| JP | 2006-068731 | A | 3/2006 |
| JP | 2006-089525 | A | 4/2006 |
| JP | 2006-342306 | A | 12/2006 |
| WO | 03/051939 | A1 | 6/2003 |
| WO | 2004/101628 | A1 | 11/2004 |
| WO | 2007/123188 | A1 | 11/2007 |
| WO | 2007/126002 | A1 | 11/2007 |
| WO | 2009/025235 | A1 | 2/2009 |
| WO | WO 2009025235 | A1 * | 2/2009 |

OTHER PUBLICATIONS

International Search Report for PCT/JP2011/066456, mailing date of Sep. 13, 2011.
International Search Report of PCT/JP2011/066455, mailing date of Sep. 13, 2011.
International Search Report of PCT/JP2011/066454, mailing date of Sep. 13, 2011.
International Search Report for PCT/JP2011/066453, mailing date of Aug. 16, 2011.
Translation of the International Preliminary Report on Patentability (PCT/IB/338) (1 page), (PCT/IB/373) (1 page) of International Application No. PCT/JP2011/066453 mailed Mar. 21, 2013 (Form PCT/ISA/237) (6 page).
Translation of the International Preliminary Report on Patentability (PCT/IB/338) (1 page), (PCT/IB/373) (1 page) of International Application No. PCT/JP2011/066455 mailed Mar. 21, 2013 (Form PCT/ISA/237) (4 page).

(Continued)

*Primary Examiner* — Ling Choi
*Assistant Examiner* — David L Miller
(74) *Attorney, Agent, or Firm* — Westerman, Hattori, Daniels & Adrian, LLP

(57) ABSTRACT

A method for producing a water-absorbent resin having a further reduced odor as compared with a water-absorbent resin obtained by a conventional method as well as a water-absorbent resin produced by the same method, by maintaining the addition rate V from the pouring nozzle for the aqueous solution of the water-soluble ethylenically unsaturated monomer in a polymerization reaction tank not more than 0.30 [$min^{-1}$], in the first stage polymerization step which is within the step of the conventional method upon performing multi-stages such as two or more stages of reversed-phase suspension polymerizations in a method for producing a water-absorbent resin, and thereby by being able to reduce the amount of the petroleum hydrocarbon dispersion medium remaining in the above water-absorbent resin.

19 Claims, No Drawings

(56) References Cited

OTHER PUBLICATIONS

International Preliminary Report on Patentability (PCT/IB/326) (1 page), (PCT/IB/373) (1 page) of International Application No. PCT/JP2011/066456 mailed Feb. 7, 2013 (Form PCT/ISA/237) (3 pages) (Japanese Only).

Translation of the International Preliminary Report on Patentability (PCT/IB/338) (1 page), (PCT/IB/373) (1 page) of International Application No. PCT/JP2011/066454 mailed Mar. 21, 2013 (Form PCT/ISA/237) (4 page).

International Preliminary Report on Patentability (PCT/IB/326) (1 page), (PCT/IB/373) (1 page) of International Application No. PCT/JP2011/066455 mailed Feb. 7, 2013 (Form PCT/ISA/237) (3 pages) (Japanese Only).

Translation of the International Preliminary Report on Patentability (PCT/IB/338) (1 pages), (PCT/IB/373) (1 page) of International Application No. PCT/JP2011/066456 mailed Mar. 21, 2013 (Form PCT/ISA/237) (4 page).

International Preliminary Report on Patentability (PCT/IB/326) (1 page), (PCT/IB/373) (1 page) of International Application No. PCT/JP2011/066453 mailed Feb. 7, 2013 (Form PCT/ISA/237) (4 pages) (Japanese Only).

International Preliminary Report on Patentability (PCT/IB/326) (1 page), (PCT/IB/373) (1 page) of International Application No. PCT/JP2011/066454 mailed Feb. 7, 2013 (Form PCT/ISA/237) (3 pages) (Japanese Only).

U.S. Office Action dated May 16, 2014, issued in related U.S. Appl. No. 13/812,753 (17 pages).

U.S. Non-Final Office Action dated Feb. 14, 2014, issued in related U.S. Appl. No. 13/812,612.

U.S. Non-Final Office Action dated Feb. 20, 2014, issued in related U.S. Appl. No. 13/812,753.

U.S. Notice of Allowance dated Jul. 2, 2014, issued in related U.S. Appl. No. 13/812,612 (25 pages).

* cited by examiner

METHOD FOR PRODUCING A WATER-ABSORBENT RESIN

TECHNICAL FIELD

The present invention relates to a method for producing a water-absorbent resin, and to a water-absorbent resin obtained by the same. More specifically, the present invention relates to a method for producing a water-absorbent resin by a reversed-phase suspension polymerization method, wherein an odor originating from a raw material component, in particular, a petroleum hydrocarbon dispersion medium, is further reduced as compared with a water-absorbent resin obtained by a conventional method, and to a water-absorbent resin obtained by the method.

BACKGROUND ART

Water-absorbent resins are widely used in hygienic materials such as disposable diapers and sanitary napkins; daily commodities such as pet sheets; water absorbing sheets for food products; industrial materials such as water blocking materials for cables; water retention agents for greening/agriculture/horticulture; and the like.

Hygienic materials such as disposable diapers and sanitary napkins are generally constituted with a top sheet, a back sheet, a hot melt adhesive, an elastic material, a water-absorbent resin and a pulp fiber, various synthetic resins and modifiers are used. Therefore, an odor originating from raw material components is perceived from the hygienic materials, in some cases. Since these hygienic materials are put on the human body, the odor makes users uncomfortable even if it is subtle and, therefore, it is desired to develop an odor-free material.

Among constituent materials of these hygienic materials, the water-absorbent resin has a subtle odor originating from the substances used in the production process, and since the odor tends to emit upon water absorption, it is considered to be desirable to reduce the odor.

As water-absorbent resins used for hygienic materials, for example, a partially-neutralized product of polyacrylic acid, a neutralized product of a starch-acrylic acid graft polymer, a hydrolysate of a starch-acrylonitrile graft copolymer, a saponified product of a vinyl acetate-acrylic acid ester copolymer are known.

As methods for producing such water-absorbent resins, an aqueous polymerization method and a reversed-phase suspension polymerization method are known. In a case where a water-absorbent resin is produced by a reversed-phase suspension polymerization method in which polymerization is performed by suspending a water-soluble monomer in a dispersion medium, a major cause of the odor is considered to originate from the dispersion medium.

As conventional methods for producing the water-absorbent resin by a reversed-phase suspension polymerization method, known are a method of polymerizing an aqueous solution of $\alpha,\beta$-unsaturated carboxylic acid and alkali metal salt thereof in a petroleum hydrocarbon solvent using a radical polymerization initiator in the presence or absence of a internal-crosslinking agent in which a sucrose fatty acid ester is used as a protective colloid agent (see Patent Document 1), and a method of polymerizing a 25% by mass or more of aqueous solution of an $\alpha,\beta$-unsaturated carboxylic acid and alkali metal salt thereof in a petroleum hydrocarbon solvent using a radical polymerization initiator in the presence or absence of a internal-crosslinking agent in which a polyglycerol fatty acid ester with an HLB of 2 to 16 is used as a surfactant (see Patent Document 2). However, these production methods do not focus on reduction of an odor, and thus odors of the resultant water-absorbent resins are not sufficiently low.

Moreover, on a purpose for reducing an odor of a water-absorbent resin, the present inventors found out that an odor originating from the dispersion medium upon water absorption can be reduced by dispersing an aqueous solution of a water-soluble ethylenically unsaturated monomer in the petroleum hydrocarbon dispersion medium to which surfactants are not added, and further adding a surfactant to the resultant dispersion liquid to further disperse and polymerize it (see Patent Document 3) in a reversed-phase suspension polymerization method; or by adding an surfactant to a dispersion liquid obtained by dispersing an aqueous solution of a water-soluble ethylenically unsaturated monomer in a petroleum hydrocarbon dispersion medium, in a first stage reversed-phase suspension polymerization upon multi-stages of two or more stages of reversed-phase suspension polymerizations (see Patent Document 4).

However, when a large amount of water-absorbent resins are used in these methods in the conventional method, an odor originating from the dispersion medium may be perceived upon water absorption, and thereby there is a need for further reducing the odor.

REFERENCE DOCUMENTS

Patent Documents

[Patent Document 1] JP-A No. 61-87702
[Patent Document 2] JP-A No. 62-172006
[Patent Document 3] WO 2007/126002
[Patent Document 4] WO 2009/025235

SUMMARY OF THE INVENTION

Problems to be Solved by the Invention

An object of the present invention relates to a method for producing a water-absorbent resin, and a water-absorbent resin obtained by the method. More specifically, an object of the present invention is to provide a method for producing a water-absorbent resin by a reversed-phase suspension polymerization method, wherein an odor originating from a raw material component, in particular, a petroleum hydrocarbon dispersion medium, is further reduced as compared with a water-absorbent resin obtained by a conventional method, and to a water-absorbent resin obtained by the method.

Means for Solving the Problems

The present inventors intensively studied about a relation between an odor originating from a petroleum hydrocarbon dispersion medium when the water-absorbent resin absorbs water, and a petroleum hydrocarbon dispersion medium used in production of the water-absorbent resin. As a result of the study, the inventors have found out that surprisingly and unexpectedly an amount of the petroleum hydrocarbon dispersion medium remaining in the above water-absorbent resin can be reduced, which has been considered to be difficult to reduce by a conventional method, to provide a method for producing a water-absorbent resin having a further reduced odor as compared with a water-absorbent resin obtained by a conventional method as well as a water-absorbent resin produced by the same method, by maintaining an addition rate V from a pouring nozzle for the aqueous solution of the water-soluble ethylenically unsaturated monomer in a polymerization reaction tank 0.30 [min$^{-1}$] or less, in the first stage polymerization step upon performing multi-stages such as two or more stages of reversed-phase suspension polymerizations in a method for producing a water-absorbent resin.

That is, the present invention relates to a method for producing a water-absorbent resin shown below, and a water-absorbent resin obtained by the method.

Item 1. A method for producing a water-absorbent resin by a multi-stage reversed-phase suspension polymerization to polymerize a water-soluble ethylenically unsaturated monomer, wherein the first stage polymerization comprising at least the following steps:
(A) performing a primary dispersion in the absence of surfactants by stirring to mix an aqueous solution of a water-soluble ethylenically unsaturated monomer containing a water-soluble radical polymerization initiator in a petroleum hydrocarbon dispersion medium in which a hydrophobic polymeric dispersion agent is dispersed or dissolved;
(B) performing a secondary dispersion by adding a surfactant to the resultant dispersion liquid; and
(C) performing a radical polymerization to obtain water-absorbent resin particles in a hydrous gel state which disperse in the petroleum hydrocarbon dispersion medium; and
the second stage polymerization comprising at least the following steps:
(D) precipitating at least a part of the surfactant;
(E) stirring to mix the aqueous solution of the water-soluble ethylenically unsaturated monomer of the second stage polymerization containing a water-soluble radical polymerization initiator therein to be absorbed and aggregated in the polymerized gel at the first stage; and
(F) performing a radical polymerization again;
wherein the aqueous solution of the water-soluble ethylenically unsaturated monomer is added in step (A) to the petroleum hydrocarbon dispersion medium at an addition rate V of 0.30 [min$^{-1}$] or less defined by the following Equation (I):

$$V = F \times A/T$$

wherein V: Addition rate [min$^{-1}$], F: Average linear flow rate from nozzle [m/min], A: Cross-sectional area of nozzle [m$^2$], and T: Total amount [m$^3$] of aqueous monomer solution added to a polymerization reaction tank.

Item 2. The method according to Item 1, wherein a post-crosslinking is performed by adding a post-crosslinking agent after completion of the multi-stage reversed-phase suspension polymerization comprising steps (A) to (F).

Item 3. The method according to Item 1 or 2, wherein a weight ratio of the amount of water-soluble ethylenically unsaturated monomers used in the second stage polymerization to the amount of water-soluble ethylenically unsaturated monomers used in the first stage polymerization, is between 1.0 and 2.0.

Item 4. The method for producing a water-absorbent resin according to any one of Items 1 to 3, wherein the surfactant is at least one kind selected from the group consisting of polyglyceryl fatty acid ester, sucrose fatty acid ester, and sorbitan fatty acid ester.

Item 5. The method for producing a water-absorbent resin according to Items 1 to 4, wherein the addition rate V from the pouring nozzle for the aqueous solution of the water-soluble ethylenically unsaturated monomer of the first stage polymerization in step (A), is within a range of 0.05 to 0.30 [min$^{-1}$].

Item 6. The method according to any one of Items 1 to 4, wherein two or more of pouring nozzles having an addition rate V of 0.3 [min$^{-1}$] or less for the aqueous solution of the water-soluble ethylenically unsaturated monomer in the first stage polymerization, are arranged in a polymerization reaction tank for performing step (A) to provide the water-soluble ethylenically unsaturated monomer.

Item 7. The method for producing a water-absorbent resin according to any one of Items 1 to 6, wherein the hydrophobic polymeric dispersion agent is at least one kind selected from the group consisting of maleic anhydride-modified polyethylene, maleic anhydride-modified polypropylene, maleic anhydride-modified ethylene-propylene copolymer, maleic anhydride-propylene copolymer, maleic anhydride-ethylene-propylene copolymer, polyethylene, polypropylene, ethylene-propylene copolymer, oxidized polyethylene, oxidized polypropylene, and an oxidized ethylene-propylene copolymer.

Item 8. The method for producing a water-absorbent resin according to any one of Items 1 to 7, wherein the water-soluble ethylenically unsaturated monomer is at least one kind selected from the group consisting of acrylic acid and its salt, methacrylic acid and its salt, and acrylamide.

Item 9. The method according to any one of Items 1 to 8, wherein the petroleum hydrocarbon dispersion medium is at least one kind selected from the group consisting of an aliphatic hydrocarbon and an alicyclic hydrocarbon, having a carbon number of 6 to 8.

Item 10. A water-absorbent resin obtained by the method according to any one of Items 1 to 9.

Effects of the Invention

According to the present invention, a method for producing a water-absorbent, wherein an odor originating from a raw material component, in particular, a petroleum hydrocarbon dispersion medium is reduced, and a water-absorbent resin obtained by the method are provided.

MODES FOR CARRYING OUT THE INVENTION

A method for producing a water-absorbent resin of the present invention comprises polymerizing a water-soluble ethylenically unsaturated monomer by a multi-stage reversed-phase suspension polymerization wherein the first stage polymerization comprising at least the following steps:
the first stage polymerization comprising at least the following steps:
(A) performing a primary dispersion in the absence of surfactants by stirring to mix an aqueous solution of a water-soluble ethylenically unsaturated monomer containing a water-soluble radical polymerization initiator in a petroleum hydrocarbon dispersion medium in which a hydrophobic polymeric dispersion agent is dispersed or dissolved;
(B) performing a secondary dispersion by adding a surfactant to the resultant dispersion liquid; and
(C) performing a radical polymerization to obtain water-absorbent resin particles in a hydrous gel state which disperse in the petroleum hydrocarbon dispersion medium; and
the second stage polymerization comprising at least the following steps:
(D) precipitating at least a part of the surfactant;
(E) stirring to mix the aqueous solution of the water-soluble ethylenically unsaturated monomer of the second stage polymerization containing a water-soluble radical polymerization initiator therein to be absorbed and aggregated in the polymerized gel at the first stage; and (F) performing a radical polymerization again;

wherein the aqueous solution of the water-soluble ethylenically unsaturated monomer is added in step (A) to the petroleum hydrocarbon dispersion medium at an addition rate V of 0.30 [min$^{-1}$] or less.

A water-absorbent resin which contains a reduced amount of a remaining petroleum hydrocarbon dispersion medium, can be obtained by the production method comprising these steps and having the above-mentioned specific addition rate V. (In the present invention, the "amount of a remaining petroleum hydrocarbon dispersion medium" (Amount of remaining dispersion medium) is a value measured by a measuring method described hereinafter.)

An origin of odor, when a water-abosorbent resin obtained by a reversed-phase suspension polymerization absorbs water, is mainly a dispersion medium remained within particles of the water-abosorbent resin. The present inventors have found out that a mechanism of a dispersion medium remaining in water-absorbent resin particles is caused by generating so-called capsule-like water-absorbent resin particles which include the dispersion medium based on generating a liquid droplet having a shape in which the disppersion medium which is an oil phase is entrapped in a liquid droplet of the aqueous monomer solution, namely, an O/W/O (oil/water/oil) type droplet, and then stabilizing and polymerizing this O/W/O type droplet itself, upon dispersing the aqueous monomer solution in the dispersion medium by means of stirring and the like.

One feature of the present invention is to comprise dispersing an aqueous solution of the water-soluble ethylenically unsaturated monomer in two steps of a "primary dispersion" in which the aqueous solution of a water-soluble ethylenically unsaturated monomer (hereinafter, "aqueous monomer solution" means the "aqueous solution of the water-soluble ethylenically unsaturated monomer" unless otherwise expressly indicated) is mixed and dispersed in a petroleum hydrocarbon dispersion medium (hereinafter, "dispersion medium" means the "petroleum hydrocarbon dispersion medium" unless otherwise expressly indicated) in the absence of surfactants in the step (A), and a "secondary dispersion" in which a surfactant is added to intend a dispersion stabilization with the surfactant in the step (B). The present invention is further to control addition speed of the aqueous monomer solution in a polymerization reaction tank which carries out the step (A) to be able to suppress generation of O/W/O type droplet as a subproduct, and thereby intended to reduce an amount of the remaining dispersion medium in the water-absorbent resin. An O/W/O type droplet is an abbreviation of (Oil in Water) in Oil, and refers to a state in which fine oil droplets are dispersed in water droplets, and the water droplets are further dispersed in an oil phase. Namely, it is constituted of an innermost oil phase, an intermediate water phase and an outermost oil phase. In the present invention, the O/W/O type droplet exhibits a state in which droplets of the aqueous solution of the monomer (water phase) contain smaller droplets of dispersion medium (oil phase).

The present inventors intensively studied about factors for generation of an O/W/O type droplet, and found out that generation of O/W/O type droplets is suppressed to reduce an amount of the remaining dispersion medium in the water-absorbent resin when the addition rate V defined in the present invention is 0.30 [min$^{-1}$] or less, under an estimation that the linear flow rate of the aqueous monomer solution upon entering and the droplet size have a relationship based on a phenomenon in which the amount of the remaining dispersion medium becomes high when the aqueous monomer solution is vigorously added through a pouring nozzle. When the addition rate V definited by the present application is evaluated, the generation of O/W/O type is suppressed at a rate of 0.30 [min$^{-1}$] or less, as a result, they found out that the amount of the remaining dispersion medium in water-absorbent resin become low.

The addition rate V is defined by the following Equation (I):

$$V = F \times A / T$$

wherein V: Addition rate [min$^{-1}$], F: Average linear flow rate from nozzle [m/min], A: Cross-sectional area of nozzle [m$^2$], and T: Total amount [m$^3$] of aqueous monomer solution added to a polymerization reaction tank.

F (Average linear flow rate from nozzle) is an index how the aqueous monomer solution vigorously rush out from an input slot (i.e., pouring nozzle). When a pump or the like is used, a value calculated from the flow rate (the volumetric flow rate is divided by cross-sectional area of a pouring nozzle output) is considered to be an average linear flow rate F from a pouring nozzle. In addition, when a pouring method using gravity and the like is adopted, a mean volumetric flow rate is determined by dividing the amount of an aqueous monomer solution to be poured by a time period for pouring to calculate the mean flow rate F.

A (Cross-sectional area of nozzle) is involved with the size of liquid mass (droplet) of the aqueous monomer solution to be poured. When the liquid mass (droplet) is large upon pouring it into a dispersion medium even if the linear flow rate of the aqueous monomer solution is low, an amount of remaining dispersion medium is large, namely, O/W/O type droplets tend to generate.

T (total amount of an aqueous monomer solution added to a polymerization reaction tank) is the amount of the aqueous monomer solution to be added which is decided depending on a size of the polymerization reaction tank, polymerization conditions and the like.

V (addition rate) is calculated by the above-mentioned equation (I), and a multiplied value of the liner flow rate F which is an index showing vigor of pouring of an aqueous monomer solution and the cross-sectional area [m$^2$] of the nozzle related to the poured liquid mass (droplet), is divided by "the total amount of the aqueous monomer solution added to a polymerization reaction tank: T [m$^3$]" as a standard, which is decided with each reactor scale to exclude the influence of the scale factor to an addition rate.

It is preferred based on experimental results that the addition rate V of the aqueous monomer solution defined in the present invention is 0.30 [min$^{-1}$] or less, more preferably the range of 0.05-0.25 [min$^{-1}$] and most preferably the range of 0.05-0.20 [min$^{-1}$]. When it is more than 0.30 [min$^{-1}$], since the reduction effect of a remaining dispersion medium deteriorates and the amount of a remaining dispersion medium increases, it is not preferred. On the other hand, when the addition rate is less than 0.05 [min$^{-1}$], the time period for adding an aqueous monomer solution is too long, and the reduction effect corresponding to spending many hours cannot be acquired, and productive efficiency becomes greatly worse, being not preferable.

When the addition rate to a polymerization reaction tank is increased while reducing the amount of the remaining dispersion medium, two or more (e.g., 2 to 3) of pouring nozzles having an addition rate of 0.30 [min$^{-1}$] or less may be arranged to perform simultaneous pouring from a plurality of nozzles, and thereby a pouring rate is increased as a whole devise. That is, as long as the addition rate V per a pouring nozzle is 0.30 [min$^{-1}$] or less, the sum of addition rates of 2 to 3 pouring nozzles may become 0.30 [min$^{-1}$] or more.

In addition, two or more pouring nozzles in which the addition rates V differ from each other may be arranged in a polymerization reaction tank. However, in this case, it is preferred to arrange nozzles as far as possible from each other from a viewpoint of reducing a remaining dispersion medium.

Examples of the water-soluble ethylenically unsaturated monomer used in the step (A) include monomers having an acid group, such as (meth)acrylic acid ["(meth)acrylic" means "acrylic" and "methacrylic", the same shall apply hereinafter], 2-(meth)acrylamide-2-methylpropanesulfonic acid and maleic acid, and salts thereof; nonionic unsaturated monomers such as (meth)acrylamide, N,N-dimethyl(meth)acrylamide, 2-hydroxyethyl (meth)acrylate and N-methylol (meth)acrylamide; and amino group-containing unsaturated monomers such as diethylaminoethyl (meth)acrylate and diethylaminopropyl (meth)acrylate, and quaternized monomers thereof. These water-soluble ethylenically unsaturated monomers may be used alone, or two or more kinds of them may be used in combination.

Among water-soluble ethylenically unsaturated monomers, (meth)acrylic acid and a salt thereof, and (meth)acrylamide are preferable from a viewpoint of industrial availability.

When the water-soluble ethylenically unsaturated monomer has an acid group, it can also be used as a salt after neutralizing the acid group.

Examples of an alkaline compound used when a monomer having an acid group is neutralized to a salt include compounds of lithium, sodium, potassium and ammonium. More specifically, examples of the alkaline compound include sodium hydroxide, potassium hydroxide, lithium hydroxide, sodium carbonate and ammonium carbonate.

When the monomer having an acid group is neutralized, a neutralization degree is preferably from 30 to 90 mol % of the acid group of the water-soluble ethylenically unsaturated monomer. When the neutralization degree is less than 30 mol %, the acid group is not easily ionized and water-absorption capacity deteriorates, and therefore it is not preferred. When the neutralization degree is more than mol %, safety issues may arise when used as hygienic materials, and therefore it is not preferred. For the timing of neutralization, it is common to perform it in a monomeric state from a viewpoint of a degree of homogeneity. However, so-called post-neutralization by adding the above alkaline compound to polymer after polymerization of monomers for neutralization, may be applied together.

In the present invention, a water-soluble ethylenically unsaturated monomer is used in a form of an aqueous solution. The concentration of the monomer in the aqueous solution of a water-soluble ethylenically unsaturated monomer is preferably from 20% by mass to saturation concentration.

If necessary, the aqueous solution of a water-soluble ethylenically unsaturated monomer may contain a chain transfer agent, a thickener and the like.

Examples of the chain transfer agent include compounds such as thiols, thiolic acids, secondary alcohols, hypophosphorous acid and phosphorous acid. These chain transfer agents may be used alone, or two or more kinds of them may be used in combination.

Examples of the thickener include carboxymethylcellulose, hydroxyethyl cellulose, hydroxypropylcellulose, methyl cellulose, polyethylene glycol, polyacrylic acid, a neutralized polyacrylate and polyacrylamide.

Examples of the petroleum hydrocarbon dispersion medium include aliphatic hydrocarbon having a carbon number of 6 to 8, such as n-hexane, n-heptane, 2-methylhexane, 3-methylhexane, 2,3-dimethylpentane, 3-ethylpentane and n-octane; alicyclic hydrocarbons having a carbon number of 6 to 8, such as cyclohexane, methylcyclohexane, cyclopentane, methylcyclopentane, trans-1,2-dimethylcyclopentane, cis-1,3-dimethylcyclopentane and trans-1,3-dimethylcyclopentane; and aromatic hydrocarbons such as benzene, toluene and xylene. Among these hydrocarbon dispersion media, aliphatic hydrocarbons having a carbon number of 6 to 8, such as n-heptane, 2-methylhexane, 3-methylhexane and n-octane; and alicyclic hydrocarbons having a carbon number of 6 to 8, such as cyclohexane, methylcyclopentane and methylcyclohexane are preferably used from viewpoints of easy industrial availability and safety. These hydrocarbon dispersion media may be used alone, or two or more kinds of them may be used in combination.

Further, among these hydrocarbon dispersion media, n-heptane and cyclohexane are preferably used from a viewpoint that a state of W/O type reversed suspension is good, suitable particle size is easily obtained, and that an industrial availability is easy and a quality is stable. As an example of a mixture of the above-mentioned hydrocarbon, a commercially available Exxsol heptane (manufactured by Exxon Mobil Co.: containing heptane and isomeric hydrocarbons of 75 to 85%) and the like may be also used to obtain a suitable result.

The amount of the petroleum hydrocarbon dispersion medium to be used is usually from 50 to 600 parts by mass, more preferably from 50 to 400 parts by mass, and still more preferably from 50 to 200 parts by mass, based on 100 parts by mass of the aqueous solution of a water-soluble ethylenically unsaturated monomer from a viewpoint of uniformly dispersing of the aqueous solution of a water-soluble ethylenically unsaturated monomer and facilitating control of the polymerization temperature.

In the step (A), when the aqueous solution of a water-soluble ethylenically unsaturated monomer is added and primarily dispersed in the petroleum hydrocarbon dispersion medium in the absence of surfactants, the amount of the remaining petroleum hydrocarbon dispersion medium can be reduced to a lower level by dispersing the water-soluble ethylenically unsaturated monomer in the presence of a hydrophobic polymeric dispersion agent.

It is preferred to select and use a hydrophobic polymeric dispersion agent which is dissolved or dispersed in the petroleum hydrocarbon dispersion medium to be used, and examples of the hydrophobic polymeric dispersion agent include those having a viscosity-average molecular weight of 20,000 or less, preferably 10,000 or less, and more preferably 5,000 or less. Specific examples thereof include maleic anhydride-modified polyethylene, maleic anhydride-modified polypropylene, a maleic anhydride-modified ethylene-propylene copolymer, a maleic anhydride-ethylene copolymer, a maleic anhydride-propylene copolymer, a maleic anhydride-ethylene-propylene copolymer, polyethylene, polypropylene, an ethylene-propylene copolymer, oxidized polyethylene, oxidized polypropylene, an oxidized ethylene-propylene copolymer, an ethylene-acrylic acid copolymer, ethyl cellulose, ethylhydroxyethyl cellulose, anhydrous maleinated polybutadiene and anhydrous maleinated EPDM (ethylene/propylene/diene terpolymer).

Among them, at least one kind selected from the group consisting of maleic anhydride-modified polyethylene, maleic anhydride-modified polypropylene, a maleic anhydride-modified ethylene-propylene copolymer, a maleic anhydride-ethylene copolymer, a maleic anhydride-propylene copolymer, a maleic anhydride-ethylene-propylene copolymer, polyethylene, polypropylene, an ethylene-propylene copolymer, oxidized polyethylene, oxidized polypropylene and an oxidized ethylene-propylene copolymer is preferred.

The amount of the hydrophobic polymeric dispersion agent to be added is preferably 5 parts by mass or less, more preferably from 0.01 to 3 parts by mass, and still more preferably from 0.05 to 2 parts by mass, based on 100 parts by mass of the aqueous solution of a water-soluble ethylenically unsaturated monomer. When the amount of the hydrophobic polymeric dispersion agent to be added is more than 5 parts by mass, it is not economic, being not preferable.

It is important that a hydrophobic polymeric dispersion agent is added to a petroleum hydrocarbon dispersion medium, and then the above dispersion medium is warmed once to establish a state where a part or whole of the hydrophobic polymeric dispersion agent is dissolved or dispersed thereafter an aqueous monomer solution is added. There is no problem even if the above dispersion medium is cooled after heating to perform an addition of the aqueous monomer solution in a state where a part or whole of the hydrophobic polymeric dispersion agent is precipitated to be dispersed in cloud state.

When the aqueous solution of a water-soluble ethylenically unsaturated monomer is added to and dispersed in the petroleum hydrocarbon dispersion medium, the aqueous solution of the water-soluble ethylenically unsaturated monomer is dispersed by stirring. However, stirring conditions vary depending on a desired dispersed droplet diameter and, therefore cannot be determined unconditionally.

The dispersed droplet diameter can be adjusted dispersed droplet diameter can be adjusted by changing a type, size, rotation numbers of a stirring impeller.

It is possible to use, as a stirring impeller, a propeller impeller, a paddle impeller, an anchor impeller, a turbine impeller, a Pfaudler impeller, a ribbon impeller, a FULLZONE impeller (manufactured by Shinko Pantech Co., Ltd.), a MAXBLEND impeller (manufactured by Sumitomo Heavy Industries, Ltd.) and Super-Mix (manufactured by Satake Chemical Equipment Mfg., Ltd.).

A surfactant is added to a primary dispersion liquid obtained in the step (A) and the aqueous solution of a water-soluble ethylenically unsaturated monomer is secondarily dispersed in the petroleum hydrocarbon dispersion medium (step (B)).

Examples of the surfactant used in the step (B) include nonionic surfactants such as sorbitan fatty acid ester, polyoxyethylene sorbitan fatty acid ester, polyglyceryl fatty acid ester, polyoxyethylene glyceryl fatty acid ester, sucrose fatty acid ester, sorbitol fatty acid ester, polyoxyethylene sorbitol fatty acid ester, polyoxyethylene alkyl ether, polyoxyethylene alkyl phenyl ether, polyoxyethylene castor oil, polyoxyethylene hydrogenated castor oil, alkyl allyl formaldehyde condensed polyoxyethylene ether, polyoxyethylene polyoxypropyl alkyl ether, polyethylene glycol fatty acid ester, alkyl glucoside, N-alkyl gluconamide, polyoxyethylene fatty acid amide and polyoxyethylene alkylamine; and anionic surfactants such as fatty acid salt, alkylbenzene sulfonate, alkylmethyl taurate, polyoxyethylene alkyl phenyl ether sulfate, polyoxyethylene alkyl ether sulfate, polyoxyethylene alkyl ether sulfonic acid and a salt thereof, polyoxyethylene alkyl phenyl ether phosphoric acid and a salt thereof, and polyoxyethylene alkyl ether phosphoric acid and a salt thereof. These surfactants may be used alone, or two or more kinds of them may be used in combination.

Among these surfactants, at least one kind selected from the group consisting of polyglyceryl fatty acid ester, sucrose fatty acid ester and sorbitan fatty acid ester are preferred from a viewpoint of dispersion stability of the aqueous solution of a water-soluble ethylenically unsaturated monomer.

The amount of the surfactant to be added in the step (B) is preferably from 0.01 to 5 parts by mass, and more preferably from 0.05 to 3 parts by mass, based on 100 parts by mass of the aqueous solution of a water-soluble ethylenically unsaturated monomer. When the amount of the surfactant to be added is less than 0.01 part by mass, dispersion stability of the aqueous monomer solution deteriorates, and therefore it is not preferred. When the amount of the surfactant to be added is more than 5 parts by mass, it is not economic, being not preferable.

A form of the surfactant added in the step (B) is not limited in particular, but a method which uses a surfactant previously diluted or dissolved in a small amount of the dispersion medium is preferred because the surfactant is dispersed and stabilized within a short period.

Besides, after adding a surfactant in the step (B), a stirring rotation number of a stirring impeller may be increased. The final dispersed droplet diameter is determined by the stirring rotation number after an increased rate to determine the particle size of the first stage polymerization.

By setting the stirring rotation number for the primary dispersion in the step (A) such that it is somewhat lower than the stirring rotation number of secondary dispersion in the step (B), it can be suppressed that a dispersion medium is included by an aqueous monomer solution droplet, and accordingly the amount of the remaining dispersion medium of water-absorbent resin can be more reduced.

The dispersion liquid obtained in the step (B) is subjected to a radical polymerization to obtain water-absorbent resin particles in a hydrous gel state, in which the water-absorbent resin is dispersed in the petroleum hydrocarbon dispersion medium (step (C)).

Examples of the water-soluble radical polymerization initiator include persulfates such as potassium persulfate, ammonium persulfate and sodium persulfate; peroxides such as hydrogen peroxide; and azo compounds such as 2,2'-azobis(2-amidinopropane)dihydrochloride, 2,2'-azobis[N-(2-carboxyethyl)-2-methylpropiondiamine]tetrahydrate, 2,2'-azobis(1-imino-1-pyrrolidino-2-methylpropane) dihydrochloride and 2,2'-azobis[2-methyl-N-(2-hydroxyethyl)-propionamide].

Among them, potassium persulfate, ammonium persulfate, sodium persulfate and 2,2'-azobis(2-amidinopropane)dihydrochloride are preferred from a viewpoint of availability and easiness of handling.

The water-soluble radical polymerization initiator may be used in combination with reducing agents such as sulfite and ascorbic acid as a redox polymerization initiator.

The amount of the water-soluble radical polymerization initiator to be used is usually from 0.01 to 1 part by mass based on 100 parts by mass of the water-soluble ethylenically unsaturated monomer. When the amount is less than 0.01 part by mass, a polymerization rate decreases, and when the amount is more than 1 part by mass, a rapid polymerization reaction arises. Therefore, both cases are not preferred.

Timing of the addition of the water-soluble radical polymerization initiator is not limited in particular, but it is preferred to previously add the water-soluble radical polymerization initiator to the aqueous solution of the water-soluble ethylenically unsaturated monomer from a viewpoint of homogeneity.

Additionally, upon a one-stage polymerization, an internal-crosslinking agent may be added to an aqueous solution of the monomer. Examples of the internal-crosslinking agent include polyols such as (poly)ethylene glycol ["(poly)" means a case where a prefix "poly" is attached or not, the same shall apply hereinafter], 1,4-butanediol, glycerol and trimethylolpropane; polyunsaturated esters having two or more vinyl groups obtained by reacting polyols with an unsaturated acid such as acrylic acid or methacrylic acid; bisacrylamides such as N,N'-methylenebisacrylamide; and polyglycidyl compounds having two or more glycidyl groups, such as (poly)ethylene glycol diglycidyl ether, (poly)ethylene glycol triglycidyl ether, (poly)glycerol diglycidyl ether, (poly)glycerol triglycidyl ether, (poly) propylene glycol polyglycidyl ether and (poly)glycerol polyglycidyl ether. These internal-crosslinking agents may be used alone, or two or more kinds of them may be used in combination.

The amount of the internal-crosslinking agent to be added is preferably 3 parts by mass or less, more preferably 1 part by mass or less, and still more preferably from 0.001 to 0.1 part by mass, based on 100 parts by mass of the water-soluble ethylenically unsaturated monomer. When the amount is more than 3 parts by mass, excess crosslinking arises and water-absorption capability excessively deteriorates, and therefore it is not preferred.

It is preferred that the internal-crosslinking agent is previously added to the aqueous solution of the water-soluble ethylenically unsaturated monomer.

The reaction temperature during reversed-phase suspension polymerization in the present invention varies depending on the kind and amount of the polymerization initiator to be used, and therefore cannot be determined unconditionally. However, it is preferably from 20 to 100° C., and more preferably from 40 to 90° C. When the reaction temperature is lower than 20° C., the degree of polymerization may decrease, and when the reaction temperature is higher than 100° C., a rapid polymerization reaction arises. Therefore, both cases are not preferred.

The size of particles after the first stage polymerization thus obtained by polymerizing water-soluble ethylenically unsaturated monomers is a median particle size preferably from 20 to 200 μm, more preferably from 30 to 150 μm, and still more preferably from 40 to 100 μm, from a viewpoint that a moderate particle size from a viewpoint of obtaining of a proper aggregated particle size in multi-stage polymerization. Besides, the median particle size of polymer particles after the first-stage polymerization is a value for particles obtained by dehydration and drying after completion of the first stage polymerization according to the following measurement method.

To the polymerization reaction liquid after completion of the above-mentioned step (C), i.e., the first stage of reversed-phase suspension polymerization, added is an aqueous solution of the water-soluble ethylenically unsaturated monomer, and subsequently the second stage of reversed-phase suspension polymerization is performed. The procedure firstly precipitates the at least partial above-mentioned surfactants after completion of the first stage (step (D)).

Surfactants lose their essential capability to stabilize an aqueous phase droplet in an oil phase (or adversely, a capability to stabilize an oil phase droplet in an aqueous phase) when they precipitate.

Examples of a precipitating method include, but not limited to, a method of decreasing a temperature of slurry after polymerization by cooling. By precipitating at least a part of surfactants before adding the aqueous solution of a water-soluble ethylenically unsaturated monomer in the second stage polymerization, the droplet of the added aqueous monomer solution is not stabilized in a dispersion medium, and is absorbed in gel-like primary particles to enhance aggregation of the primary particles and thereby, a particle diameter suitable for use in hygienic materials is obtained. In addition, due to precipitation of the surfactants, generation of new O/W/O type droplets upon adding the aqueous monomer solution of the second stage polymerization is suppressed to prevent increase in an amount of the remaining dispersion medium. Therefore obtained water absorbent resin has lower amount of remaining dispersion medium than that involved in the first stage polymerization, because amount of water absorbent resin substantially increases through the second stage polymerization which hardly increase in an amount of remaining dispersion medium. In addition, the hydrophobic polymeric dispersion agent dissolving together with the surfactant may precipitate into the dispersion medium because the dispersion agent becomes impossible to be dissolved in a dispersion medium by cooling.

After precipitating at least a part of the surfactants, the aqueous solution of the water-soluble ethylenically unsaturated monomer in the second stage polymerization containing a water-soluble radical polymerization initiator is stirred to mix therein to absorb and aggregate the first stage of polymerization gel (step (E)).

It is possible to use, as water-soluble ethylenically unsaturated monomer at the second-stage reversed-phase suspension polymerization, the same as those exemplified as the water-soluble ethylenically unsaturated monomer for the first stage polymerization. Kinds, neutralization degree and neutralized salt of the monomer, and the concentration of the aqueous monomer solution may be the same as or different from those of the water-soluble ethylenically unsaturated monomer in the first stage polymerization.

The polymerization initiator to be added to an aqueous solution of a water-soluble ethylenically unsaturated monomer in the second stage polymerization, any one may be selected from those exemplified as the polymerization initiator used in the first stage polymerization to use.

If necessary, an internal-crosslinking agent and a chain transfer agent may also be added to the aqueous solution of a water-soluble ethylenically unsaturated monomer in the second stage polymerization, and any one may be selected from those exemplified for the first stage polymerization to use.

The amount of the water-soluble ethylenically unsaturated monomer to be added in the second stage polymerization is preferably from 1.0 to 2.0-fold, and more preferably from 1.1 to 1.8-fold, based on the amount of the water-soluble ethylenically unsaturated monomer in the first stage polymerization from viewpoints of obtaining appropriate aggregated particles and reducing the amount of the remaining dispersion medium. When the amount of the water-soluble ethylenically unsaturated monomer to be added is less than 1.0-fold, the reduction effect by the amount of the remaining dispersion medium is low, being not preferable because the amount to be obtained decreases. When the amount of the water-soluble ethylenically unsaturated monomer to be added is more than 2.0-fold, aggregated particles having a proper median particle size are not obtained, being not preferable because particles polymerized in the first stage polymerization cannot absorb fully the aqueous monomer solution in the second stage polymerization to cause fine powders.

In addition, the addition rate V from the pouring nozzle for the aqueous solution of a water-soluble ethylenically unsaturated monomer in the second stage polymerization may be 0.30 [min$^{-1}$] or less similarly to the addition rate in the first stage polymerization.

It is sufficient that the entire components are mixed uniformly by stirring in the second stage of the reversed-phase suspension polymerization. The median particle size of aggregated particles may be controlled depending on a precipitation state of the surfactants and a ratio of the amount of the ethylenically unsaturated monomer in the second stage polymerization to the ethylenically unsaturated monomer in the first stage polymerization.

Additionally, the median particle size of the aggregated particles suitable for use in hygienic materials is preferably from 200 to 600 μm, more preferably from 250 to 500 μm, and still more preferably from 300 to 450 μm.

After adding the aqueous monomer solution for a second stage polymerization, polymerization is performed by a radical polymerization (step (F)).

The reaction temperature in reversed-phase suspension polymerization in the second stage polymerization cannot be determined unconditionally because it depends on the kind and amount of the polymerization initiator. However, it is preferably from 20 to 100° C., and more preferably from 40 to 90° C.

Furthermore, for the purpose of improving productivity, multi-stage reversed-phase suspension polymerization may be performed by performing a third or later stage polymerization reaction similar to the second stage reversed-phase suspension polymerization.

After completion of these multi-stages of reversed-phase suspension polymerization, it is preferred to add a post-crosslinking agent containing two or more functional groups having reactivity with a functional group derived from a water-soluble ethylenically unsaturated monomer. The crosslinking density of the surface layer of water-absorbent resin particles and various properties such as water-absorption capacity under load, water-absorption rate and gel strength can be enhanced by adding post-crosslinking agent after the polymerization for reaction, and to impart properties suitable for use in hygienic materials.

A post-crosslinking agent to be used in the post-crosslinking reaction is not particularly limited as long as it can react with a functional group derived from the water-soluble ethylenically unsaturated monomer used in the polymerization.

Examples of the post-crosslinking agent to be used include polyols such as ethylene glycol, propylene glycol, 1,4-butanediol, trimethylolpropane, glycerol, polyoxyethylene glycol, polyoxypropylene glycol and polyglycerol; polyglycidyl compounds such as (poly)ethylene glycol diglycidyl ether, (poly)ethylene glycol triglycidyl ether, (poly)glycerol diglycidyl ether, (poly)glycerol triglycidyl ether, (poly)propylene glycol polyglycidyl ether and (poly)glycerol polyglycidyl ether; haloepoxy compounds such as epichlorohydrin, epibromohydrin and α-methylepichlorohydrin; compound having two or more reactive functional groups, for example, isocyanate compounds such as 2,4-tolylene diisocyanate and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol and 3-butyl-3-oxetane ethanol; oxazoline compounds such as 1,2-ethylenebisoxazoline; and carbonate compounds such as ethylene carbonate. These post-crosslinking agents may be used alone, or two or more kinds of them may be used in combination.

Among them, polyglycidyl compounds such as (poly)ethylene glycol diglycidyl ether, (poly)ethylene glycol triglycidyl ether, (poly)glycerol diglycidyl ether, (poly)glycerol triglycidyl ether, (poly)propylene glycol polyglycidyl ether and (poly)glycerol polyglycidyl ether are preferred from a viewpoint of excellent reactivity.

The amount of the post-crosslinking agent to be added is preferably from 0.01 to 5 parts by mass, and more preferably from 0.02 to 3 parts by mass, based on 100 parts by mass of the total amount of the water-soluble ethylenically unsaturated monomer subjected to the polymerization. When the amount of the post-crosslinking agent to be added is less than 0.01 part by mass, it is impossible to enhance various properties such as water-absorption capacity under load, water-absorption rate and gel strength of the resultant water-absorbent resin, and when the amount to be added is more than 5 parts by mass, water-absorption capacity excessively deteriorates. Therefore both cases are not preferred.

The post-crosslinking agent may be added as it is, or added in a form of an aqueous solution. If necessary, the post-crosslinking agent may be added in a form of an aqueous solution containing a hydrophilic organic solvent. Examples of the hydrophilic organic solvent include lower alcohols such as methyl alcohol, ethyl alcohol, n-propyl alcohol, isopropyl alcohol and propylene glycol; ketones such as acetone and methyl ethyl ketone; ethers such as diethyl ether, dioxane and tetrahydrofuran; amides such as N,N-dimethylformamide; and sulfoxides such as dimethyl sulfoxide. These hydrophilic organic solvents may be used alone, or two or more kinds of them may be used in combination. Alternatively, these hydrophilic organic solvents may be used as a mixed solvent with water.

The timing of the addition of the post-crosslinking agent may be after completion of the polymerization and is not particularly limited. The post-crosslinking reaction is preferably performed in a dehydration or drying step after the polymerization in the presence of water at an amount within a range from 1 to 200 parts by mass, more preferably from 5 to 100 parts by mass, and still more preferably from 10 to 50 parts by mass, based on 100 parts by mass of the water-absorbent resin. By adjusting the amount of water during the addition of the post-crosslinking agent, post-crosslinking in the surface layer of particles of the water-absorbent resin can be more suitably performed and excellent water-absorption capability can be exhibited.

The temperature in the post-crosslinking reaction is preferably from 50 to 250° C., more preferably from 60 to 180° C., still more preferably from 60 to 140° C., and even more preferably from 70 to 120° C.

In the present invention, a drying step may be performed under a normal pressure or reduced pressure, or may be performed under a gas flow such as nitrogen gas flow in order to enhance drying efficacy. When the drying step is performed under a normal pressure, the drying temperature is preferably from 70 to 250° C., more preferably from 80 to 180° C., still more preferably from 80 to 140° C., and even more preferably from 90 to 130° C. When the drying step is performed under reduced pressure, the drying temperature is preferably from 60 to 100° C., and more preferably from 70 to 90° C.

The water content of the water-absorbent resin after drying is 20% by mass or less, and usually preferably 10% by mass or less, in a viewpoint of imparting fluidity. Inorganic lubricant agents such as an amorphous silica powder and the like may also be added to the water-absorbent resin so as to improve fluidity.

EXAMPLES

The present invention will be described in detail by way of Examples, Comparative Examples and the like, but the present invention is not limited only to these Examples.

The median particle size, the water content, and the amount of the remaining dispersion medium (amount of petroleum hydrocarbon dispersion medium remaining in water-absorbent resin particles) of water-absorbent resins obtained in the respective Examples and Comparative Examples were evaluated by the following methods.

(1) Median Particle Size

A water-absorbent resin (50 g) was passed through a JIS standard sieve having a sieve opening size of 250 μm. The median particle size was measured using a combination of sieves I) when 50% by mass or more of the resin remaining on the sieve, while using a combination of sieves II) when less than 50% by mass of the resin remaining on the sieve.

I) JIS standard sieves were combined in a downward order of; a sieve having a sieve opening size of 850 μm, a sieve having a sieve opening size of 600 μm, a sieve having a sieve opening size of 500 μm, a sieve having a sieve opening size of 425 μm, a sieve having a sieve opening size of 300 μm, a sieve having a sieve opening size of 250 μm, a sieve having a sieve opening size of 150 μm and a tray.

II) JIS standard sieves were combined in a downward order of; a sieve having a sieve opening size of 425 μm, a sieve having a sieve opening of 250 μm, a sieve having a sieve opening size of 180 μm, a sieve having a sieve opening size of 150 μm, a sieve with a sieve opening size of 106 μm, a sieve with a sieve opening size of 75 μm, a sieve having a sieve opening size of 45 μm and a tray.

About 50 g of the water-absorbent resin was placed on the uppermost sieve of the combination, and classified for 20 minutes using a Rotap-type shaking machine.

After the sieve classification, the mass of the water-absorbent resin remaining on the respective sieves was calculated in terms of mass % based on the total mass of resin, the values were integrated in an order from the resins with a larger particle size, and thereby the relations between the sieve openings and integration values of the mass % of the water-absorbent resin remaining on the sieve were plotted on a logarithmic-probability paper. The plots on the logarithmic-probability paper were connected with a straight line, and the particle size corresponding to integrated mass % of 50% by mass was defined as the median particle size.

(2) Water Content

About 2.5 g of the water-absorbent resin was accurately weighed (X g) into an aluminium cup, and after drying at 105° C. with a hot air dryer for 2 hours, the mass of the dried water-absorbent resin was measured (Y g), and then the water content was calculated by the following equation. Besides, it is assumed that tare mass of the aluminium cup does not change before and after drying.

Water content(%)=$(X-Y)/X \times 100$ (3) Amount of Remaining Dispersion Medium

In order to more fully extract the amount of the remaining dispersion medium from the water-absorbent resin charged in the sample bottle relative to the conventional measuring method of Patent Document 4 and the like such that measurement of the amount of the remaining dispersion medium at a lower level may be enabled, it is improved as follows such that swelling magnification is raised, and phosphoric acid is added to easily dissolve a swelling gel.

(a) Formation of Calibration Curve

Approximate 10 g of the petroleum hydrocarbon dispersion medium (hereinafter referred to as a "dispersion medium") used to polymerize a sample for measuring a remaining dispersion medium, is placed into a screw vial or the like to cool the vial with an ice-water bath. Similarly, 100 g of DMF (dimethylformamide) and 60 g of 25% by mass of an aqueous phosphoric acid solution used for the measurement, were also cooled with an ice-water bath. (Charging is performed after sufficiently cooling because of transpiration inhibition for the dispersion medium during charging.)

0.2 g of the above dispersion medium was accurately weighed into a 50 ml volumetric screw vial and then the above cooled DMF was added thereto to accurately make 20 g, followed by stirring with a magnetic stirrer bar to obtain Standard sample solution 1. This Standard sample solution 1 was also cooled with an ice-water bath.

0.2 g of the above Standard sample solution 1 was then accurately weighed into a 50 ml volumetric screw vial and the above cooled DMF was added thereto to accurately make 20 g, followed by stirring with a magnetic stirrer bar to obtain Standard sample solution 2.

This Standard sample solution 2 was also cooled with an ice-water bath.

In a 20 ml volumetric vial bottle (No. 5, manufactured by Maruemu Corporation), 0.02, 0.05, 0.1 or 0.5 g of the above Standard sample solution 2 and 0.02 g of the above Standard sample solution 1 were accurately weighed and the cooled DMF was added thereto to make the amount of contents in each vial bottle to a total amount of 3.8 g (4 ml). Furthermore, each vial bottle was charged with 5 ml of 25% by mass of the aqueous phosphoric acid solution, sealed and tightened with a septum rubber and an aluminium cap, and then stirring was performed by shaking each the bottle.

In addition, attention has been paid to perform quickly procedures from charging of the sample into the 20-ml volumetric vial to the sealing, to prevent a dispersion medium from transpiring from the vial as possible. Moreover, attention has been paid also to fully cool DMF and 25% by mass of an aqueous phosphoric acid solution such that the dispersion medium did not transpire due to development of heat at the time of mixing the both reagents, and to fully mix them after sealing with an aluminium cap or the like.

This vial bottle was warmed at 110° C. for 2 hours, and 1 ml of a vapor phase portion was collected such that the vapor phase portion was not cooled, and then it was injected into a gas chromatograph to obtain a chromatogram.

(Use of Head Space Autosampler)

The concentrations of the above Standard sample solutions were calculated based on amount to be charged, and then the amount to be charged of the dispersion medium in each vial bottle was calculated to prepare a calibration curve based on the amount to be charged and a peak area of the chromatogram. When a mixture of petroleum hydrocarbons was used as the dispersion medium, plural peaks appeared and therefore a calibration curve was prepared based on a total value of the peak areas and the charge amount.

(b) Measurement of Amount of Dispersion Medium Remaining in Sample

About 2 g of a sample to be measured was charged into an aluminium cup and then dried with a hot air dryer at 105° C. for 2 hours to adjust the water content.

Required amounts of DMF and 25% by mass of an aqueous phosphoric acid solution used for the measurement, were also charged into a screw bottle, and cooled with an ice-water bath.

Into a 20 ml volumetric vial bottle (No. 5, manufactured by Maruemu Corporation), 0.10 g of the above sample was accurately weighed, and the bottom of the vial bottle was dipped in an ice bath to cool the vial bottle and the water-absorbent resins. To this vial bottle were added 4 ml of the above cooled DMF and, further 5 ml of 25% by mass of the above cooled aqueous phosphoric acid solution. The vial bottle was quickly tightened by sealing with a septum rubber and an aluminium cap and, then gently shaken to mix. After allowing to stand for 10 min, it was confirmed that the water-absorbent resin in the vial bottle was swelled, the vial bottle was vigorously shaken to agitate the inside strongly. This vial bottle was pre-heated at 110° C. for 2 hours to strongly agitate the inside again after heating.

In addition, attention has been paid to perform quickly procedures from charging of the sample into the 20-ml volumetric vial to the sealing, to prevent a dispersion medium from transpiring from the vial as possible as much as possible.

This vial bottle was warmed at 110° C. for 2 hours, and 1 ml of a vapor phase portion was collected such that the vapor phase portion was not cooled, and then it was injected into a gas chromatograph to obtain a chromatogram.
(Use of Head Space Autosampler)

The amount of the dispersion medium contained in the amount (0.10 g of observed values) of the charged sample was calculated from the calibration curve made based on the peak area of the resultant chromatogram, and then converted into the amount [ppm] of the dispersion medium contained per 1 g of the sample.

Moreover, each of Examples and Comparative Examples was performed 3 times, and the amount of the remaining dispersion medium of each group was shown as Mean±Standard deviation.

Statistical evaluation of differences between each groups was performed using Student's t-test (** shows p<0.01).

The conditions of a gas chromatograph used in the measurement of the amount of the remaining dispersion medium in the present invention are as follows.
  Model: GC-14A+HSS2B (HEADSPACE Autosampler) manufactured by Shimadzu Corporation
  Filler: Squalane 25% Shimalite (NAW) (101) 80-100 mesh
  Column: 3.2 mm in diameter×2 m
  Column temperature: 80° C.
  Injection port temperature: 180° C.
  Detector temperature: 180° C.
  Detector: FID
  Gas carrier: Nitrogen gas
  $V_i$al bottle heating temperature: 110° C.
  Syringe setting temperature: 110° C.
(c) Comparison with Conventional Measuring Method As a result of measuring the amount of the remaining dispersion medium for the same sample, the above-mentioned measuring method of the present application could have measured the amount of the remaining dispersion medium by high sensitivity more as compared with the conventional method of Patent Document 4. For example, for Comparative Example 2 of the present invention, while the measuring method of the present invention exhibits 104 ppm of the amount of the remaining dispersion medium, the conventional method inhibits only 81 ppm of the amount of the remaining dispersion medium.
(d) Measurement of Amount of Dispersion Medium Dissolved in Aqueous Monomer Solution in the Absence of Surfactants and the Like The following experiment was conducted for the purpose of investigating the amount of dispersion medium dissolved in an aqueous monomer solution in the absence of surfactants and the like.

REFERENCE EXPERIMENTAL EXAMPLE

A measurement of a dissolved amount of a dispersion medium in an aqueous solution of the water-soluble ethylenically unsaturated monomer was performed by the following procedures:
  1) Into a 500 mL Erlenmeyer flask, 46.0 g of 80% by mass of acrylic acid was charged and neutralized by adding dropwise 51.1 g of 30% by mass sodium hydroxide under stirring while cooling the flask from the outside. To this were added 21.9 g of ion exchange water to prepare an aqueous solution of a water-soluble ethylenically unsaturated monomer (the aqueous monomer solution having a neutralization degree of 75 mol % and a concentration of 38% by mass).
  2) In a 2 L volumetric five-necked cylindrical separable round-bottom flask (hereinafter referred to as a "round-bottom flask") equipped with a stirrer with two steps of 50 mm in diameter pitched blade paddle impellers, a thermometer and a cooling tube, 171 g of n-heptane was weighted.
  3) The above-mentioned round bottom flask was dipped in a water bath, and n-heptane was agitated at 500 rpm, and maintained to an inside temperature of 40±1° C.
  4) The acrylic acid neutralization aqueous solution prepared in Procedure 1) was supplied, and the temperature of the water bath was adjusted to maintain the temperature such that it becomes an inside temperature of 40±1° C. while stirring at 500 rpm for 30 minutes.
  5) After stirring for 30 minutes, the stirrer is stopped, and the round bottom flask is allowed to stand for minutes while maintaining the same water bath temperature.
  6) Only lower layer neutralization liquid layer was gently withdrawn such that two-layer separation is not mixed.
  7) According to the measuring method of the amount of remaining dispersion medium, about 0.26 g (corresponding to about 0.1 g in the amount of the monomer) of the neutralized liquid withdrawn in 20 mL volumetric vial bottle was accurately weighted to add cooled DMF and phosphoric acid solution.
  8) After sealing with a vial cap and stirring, preheating at 110° C. for 2 hours is performed, and according to the measuring method of the amount of remaining dispersion medium, the amount of n-heptane in the neutralized liquid was measured.

The first polymerization condition in Examples of the present application, namely, the amount of amount of n-heptane (dispersion medium) dissolved into the acrylic acid neutralization aqueous solution (aqueous monomer solution) at the time of stirring by the first stage of polymerization conditions of a statement, i.e., 40° C., at 500 rpm The conditions for the first stage polymerization described in Examples of the present application, namely, the amount of n-heptane (dispersion medium) dissolved in the acrylic acid neutralization aqueous solution (aqueous monomer solution) when stirring at 500 rpm and 40° C., was 80 ppm on the monomer basis. Therefore, this amount (80 ppm) of the dispersion medium was considered to be the minimum amount of the remaining dispersion medium which can be reduced by the conventional method (in Patent Document 4 and the like).

Comparative Example 1

The example 7 of WO2009/025235 (Patent document 4) was performed as Comparative Example 1.

Namely, into a 500 mL Erlenmeyer flask, 92.0 g of 80% by mass of acrylic acid was charged and neutralized by adding dropwise 102.2 g of 30% by mass sodium hydroxide under stirring while cooling the flask from the outside. To this were added 0.11 g of potassium persulfate, 8.3 mg of ethylene glycol diglycidyl ether and 43.6 g of ion-exchange water to prepare an aqueous solution of a water-soluble ethylenically unsaturated monomer (hereinafter referred to as "aqueous monomer solution").

In a 2 L volumetric five-necked cylindrical round-bottom separable flask (hereinafter referred to as a "round-bottom flask") equipped with a stirrer having a two-stage pitched blade paddle impellers of 50 mm in diameter, a thermometer, a reflux condenser and a nitrogen gas introducing tube, 334 g of n-heptane was weighted as a petroleum hydrocarbon dispersion medium. To the round-bottom flask was added 0.92 g of a maleic anhydride-modified ethylene-propylene copolymer (manufactured by Mitsui Chemicals, Inc., trade name: HIWAX 1105A) as a hydrophobic polymeric dispersion agent, and then this was warmed up to 75 to 80° C. with a water bath at 85° C. at a stirring rate of 300 rpm to dissolve and disperse it before air cooling to an inner temperature of 61° C. The above-mentioned aqueous monomer solution was charged once into the above heptane while stirring them at 300 rpm by using a funnel made of SUS, having an inside diameter of 8 mm at opening at the tip. When a time period required from the start to the end for providing the aqueous monomer solution was measured by using a stopwatch, the time period was 12 seconds. By converting the aqueous monomer solution 238 g by the specific gravity of 1.15 g/ml, and dividing a volume of 207 ml by 12 sec to obtain a mean volume flow rate of 17.3 ml/sec, Cross-sectional area $A=\pi/4 \times 0.8$ [cm]$\times 0.8$ [cm]$=0.503$ [cm$^2$]$=5.03 \times 10^{-5}$ [m$^2$], Linear flow rate $F=17.3$ [ml/sec]/0.503 [cm$^2$]$\times 60$ [sec/min]$\times 0.01$ [m/cm]$=20.6$ [m/min], and Addition rate $V=F$[m/min]$\times 100$ [cm/m]$\times A$[cm$^2$]/207 [ml]$=5.0$ [min$^{-1}$]. After adding the aqueous monomer solution, it was agitated at an inner temperature of 40° C. for 10 minutes and primarily dispersed. (step (A))

Next, a solution separately prepared by warming 0.92 g of a sucrose fatty acid ester (manufactured by Mitsubishi-Kagaku Foods Corporation, trade name: S-370) as a surfactant to dissolve it in 8.28 g of n-heptane by warming at 60° C. or higher was added to the round-bottom flask through a funnel and then a stirring rate was increased to 500 rpm to secondly disperse the aqueous monomer solution. (step (B))

The atmosphere in the system was well substituted with nitrogen while maintaining the inner temperature of the round-bottom flask containing the dispersion at 40° C., and a radical polymerization reaction was performed by warming for 1 hour with a hot water bath at 70° C. (step (C))

After completion of the first stage polymerization, the stirring rate was increased to 1,000 rpm and the inner temperature was cooled to near 25° C. to precipitate at least a part of the surfactant. (step (D))

Separately, to a 500 mL Erlenmeyer flask, 128.8 g of 80 mass % acrylic acid was added and neutralized by adding dropwise 142.9 g of 30 mass % sodium hydroxide under stirring while cooling the flask from the outside. To this were added 0.15 g of potassium persulfate, 11.6 mg of ethylene glycol diglycidyl ether and 16.7 g of distilled water to prepare an aqueous monomer solution for the second stage polymerization. Next, the aqueous monomer solution for the above-mentioned second stage polymerization was added to the cooled polymerization liquid (after step (D)) by full opening the cock part of a dropping funnel having an inside diameter of 4.5 mm at an addition opening, stirred to mix for some time, and absorbed into a polymerization gel at the first stage. The time period required to add an aqueous monomer solution at this time is 55 seconds, and by converting the aqueous monomer solution of 288.6 g by the specific gravity of 1.17 g/ml, and dividing the volume of 246.7 ml by 55 seconds to obtain Mean volume flow rate of 4.49 ml/sec at the pouring time, Cross-sectional area $A=\pi/4 \times 0.45$ [cm]$\times 0.45$ [cm]$=0.159$ [cm$^2$]$=1.59 \times 10^{-5}$ [m$^2$], Linear flow rate $F=4.49 \times$ [ml/sec]/0.159 [cm$^2$]$\times 60$/[sec/min]$\times 0.01$ [m/cm]$=16.84$ [m/min], Addition rate $V=F$[m/min]/100 [cm/m]$\times A$[cm$^2$]/246.7 [ml]$=1.09$ [min$^{-1}$]. (step (E))

Subsequently, the atmosphere in the system was well substituted with nitrogen while maintaining the inner temperature of the round-bottom flask containing the above dispersion liquid near room temperature, and a radical polymerization reaction was performed by warming for 1 hour with a hot water bath at 70° C. (step (F))

After the polymerization reaction in the second stage, the reaction suspension was heated using an oil bath at 120° C. and about 260 g of water was removed off from the system by azeotropic distillation while refluxing heptane in the flask to obtain a dehydrated polymer dispersed in heptane. To the resultant heptane dispersed dehydrated polymer, 8.2 g of a 2% aqueous solution of ethylene glycol diglycidyl ether as a post-crosslinking agent was added and the post-crosslinking reaction was performed at 83° C. for 2 hours.

Then, heating is performed using an oil bath at 120° C., n-heptane and water were removed off from the system by distillation, followed by drying under a nitrogen gas flow to obtain 237 g of a water-absorbent resin having in a form of aggregated spherical particles by passing through a sieve of 850 µm. This water-absorbent resin had a median particle size of 372 µm, and a water content of 4.8%. (The median particle size of the primary particles of this water-absorbent resin is about 60 µm.)

Comparative Example 2

The example 8 of WO2009/025235 (Patent document 4) was performed as Comparative Example 2. (The example is an example with the lowest amount of the remaining dispersion medium in Patent Document 4.) According to the same manner as that of Comparative Example 1, except that in step (A) of Comparative Example 1, 0.46 g of an oxidized ethylene-propylene copolymer (manufactured by Mitsui Chemicals, Inc., trade name: HIWAX 4052E) and 0.46 g of a maleic anhydride-modified ethylene-propylene copolymer (manufactured by Mitsui Chemicals, Inc., trade name: HIWAX 1105A) were used substituted for 0.92 g of a maleic anhydride-modified ethylene-propylene copolymer (manufactured by Mitsui Chemicals, Inc., trade name: HIWAX 1105A) as a hydrophobic polymeric dispersion agent, and this was warmed up to 83 to 86° C. with a water bath at 90° C., 235 g of a water-absorbent resin having in a form of aggregated spherical particles was obtained. This water-absorbent resin had a median particle size of 356 µm, and a water content of 4.5%.

Example 1

The addition method of the aqueous monomer solution in Comparative Example 1 (Patent Document 4, Example 7) was changed into within the range of an addition rate described in the present application as Example 1. Specifically, into a 500 mL Erlenmeyer flask, 92.0 g of 80% by mass of acrylic acid was charged and neutralized by adding dropwise 102.2 g of 30% by mass sodium hydroxide under stirring while cooling the flask from the outside. To this were added 0.11 g of potassium persulfate, 8.3 mg of ethylene glycol diglycidyl ether and 43.6 g of ion-exchange water to prepare an aqueous solution of a water-soluble ethylenically unsaturated monomer.

In a 2 L volumetric six-necked round-bottom flask equipped with a stirrer having a two-stage pitched blade paddle impellers of 50 mm in diameter, a thermometer, a reflux condenser and a nitrogen gas introducing tube, 334 g of n-heptane was weighted as a petroleum hydrocarbon dispersion medium. To the round-bottom flask was added 0.92 g of a maleic anhydride-modified ethylene-propylene copolymer (manufactured by Mitsui Chemicals, Inc., trade name: HIWAX 1105A) as a hydrophobic polymeric dispersion agent, and then this was warmed up to 75 to 80° C. with a water bath at 85° C. at a stirring rate of 300 rpm to dissolve and disperse it before air cooling to an inner temperature of 61° C.

A nozzle (made by fluororesin tube with an inside diameter of 1 mm) with an inside diameter of 1 mm was attached to the tip of the tube of the tube pump (MASTERFLEX L/S series) previously prepared, the nozzle is fixed to a opening at the six openings of the separable cover, and the above-mentioned aqueous solution of the water-soluble ethylenically unsaturated monomer was added to the above-mentioned heptane stirring at 300 rpm (while keeping in mind that an aqueous monomer solution is not contacted with the wall surface) in a pump flow rate of 21 ml/min (observed separately). (The addition of the total amount of the above-mentioned aqueous monomer solution required about 600 seconds.) From Cross-sectional area $A=\pi/4 \times 0.1 \times 0.1 = 7.85 \times 10^{-3}$ $[m^2] = 7.85 \times 10^{-7}$ $[m^2]$ and Linear flow rate $F=21$ $[ml/min]/(7.85 \times 10^{-3}$ $[m^2]) \times 0.01$ $[m/cm] = 26.8$ $[m/min]$, Addition rate $V=F[m/min] \times 100$ $[cm/m] \times A[cm^2]/207$ $[ml] = 0.10$ $[min^{-1}]$ was calculated at this time. After adding the aqueous monomer solution, it was agitated at an inner temperature of 40° C. for 10 minutes and primarily dispersed. (step (A))

Next, a solution separately prepared by warming 0.92 g of a sucrose fatty acid ester (manufactured by Mitsubishi-Kagaku Foods Corporation, trade name: S-370) as a surfactant to dissolve it in 8.28 g of n-heptane by warming at 60° C. or higher was added to the round-bottom flask through a funnel and then a stirring rate was increased to 500 rpm to secondly disperse the aqueous monomer solution. (step (B))

Next, the atmosphere in the system was well substituted with nitrogen while maintaining the inner temperature of the round-bottom flask containing the dispersion at 40° C., and a radical polymerization reaction was performed by warming for 1 hour with a hot water bath at 70° C. (step (C))

After completion of the first stage polymerization, the stirring rate was increased to 1,000 rpm and the inner temperature was cooled to near 25° C. to precipitat at least a part of the surfactant. (step (D))

Separately, to a 500 mL Erlenmeyer flask, 128.8 g of 80 mass % acrylic acid was added and neutralized by adding dropwise 142.9 g of 30 mass % sodium hydroxide under stirring while cooling the flask from the outside. To this were added 0.15 g of potassium persulfate, 11.6 mg of ethylene glycol diglycidyl ether and 16.7 g of distilled water to prepare an aqueous monomer solution in the second stage polymerization. Next, a nozzle (made by fluororesin tube with an inside diameter of 1 mm) with an inside diameter of 1 mm was attached to the tip of the tube of the tube pump (MASTERFLEX L/S series) previously prepared, the nozzle is fixed to a opening at the six openings of the separable cover, and the above-mentioned aqueous solution of the water-soluble ethylenically unsaturated monomer was added to the above-mentioned heptane stirring at 1000 rpm (while keeping in mind that an aqueous monomer solution is not contacted with the wall surface) in a pump flow rate of 25 ml/min (observed separately). (The addition of the total amount of the above-mentioned aqueous monomer solution required about 600 seconds.) From the volume being 246.7 ml by converting the aqueous monomer solution of 288.6 g by the specific gravity of 1.17 g/ml, and Cross-sectional area $A=\pi/4 \times 0.1 \times 0.1 = 7.85 \times 10^{-3}$ $[m^2] = 7.85 \times 10^{-7}$ $[m^2]$, and Linear flow rate $F=25$ $[ml/min]/(7.85 \times 10^{-3}$ $[m^2]) \times 0.01$ $[m/cm] = 31.8$ $[m/min]$, at this time, Addition rate $V=F[m/min] \times 100$ $[cm/m] \times A[cm^2]/246.7$ $[ml] = 0.10$ $[min^{-1}]$. (step (E))

Next, the atmosphere in the system was well substituted with nitrogen while maintaining the inner temperature of the round-bottom flask containing the above dispersion liquid near room temperature, and a radical polymerization reaction was performed by warming for 1 hour with a hot water bath at 70° C. (step (F))

After the polymerization reaction in the second stage, the reaction suspension was heated using an oil bath at 120° C. and about 260 g of water was removed off from the system by azeotropic distillation while refluxing heptane in the flask to obtain a dehydrated polymer dispersed in heptane. To the resultant heptane dispersed dehydrated polymer, 8.2 g of a 2% aqueous solution of ethylene glycol diglycidyl ether as a post-crosslinking agent was added and the post-crosslinking reaction was performed at 83° C. for 2 hours.

Then, heating is performed using an oil bath at 120° C., n-heptane and water were removed off from the system by distillation, followed by drying under a nitrogen gas flow to obtain 237 g of a water-absorbent resin having in a form of aggregated spherical particles by passing through a sieve of 850 µm. This water-absorbent resin had a median particle size of 363 µm, and a water content of 5.8%.

Example 2

The addition method of the aqueous monomer solution in Comparative Example 2 (Patent Document 4, Example 8) was changed into within the range of an addition rate described in the present application to make Example 2.

According to the same manner as that of Example 1, except that in step (A) of Example 1, 0.46 g of an oxidized ethylene-propylene copolymer (manufactured by Mitsui Chemicals, Inc., trade name: HIWAX 4052E) and 0.46 g of a maleic anhydride-modified ethylene-propylene copolymer (manufactured by Mitsui Chemicals, Inc., trade name: HIWAX 1105A) were used substituted for 0.92 g of a maleic anhydride-modified ethylene-propylene copolymer (manufactured by Mitsui Chemicals, Inc., trade name: HIWAX 1105A) as a hydrophobic polymeric dispersion agent, and this was warmed up to 83 to 86° C. with a water bath at 90° C., 236 g of a water-absorbent resin having in a form of aggregated spherical particles was obtained. This water-absorbent resin had a median particle size of 341 µm, and a water content of 4.7%.

Comparative Example 3

In Example 1, two-step dispersion (primary and secondary dispersion) of the aqueous monomer solution for the first stage polymerization, which is the feature of the present invention, was not performed as Comparative Example 3.

Specifically, after preparing the aqueous monomer solution for the first stage polymerization according to the same manner as in Example 1, in a 2 L volumetric six-necked round-bottom flask equipped with a stirrer having a two-stage pitched blade paddle impellers of 50 mm in diameter, a thermometer, a reflux condenser and a nitrogen gas introducing tube, 342 g of n-heptane was weighted as a petroleum hydrocarbon dispersion medium. To the round-bottom flask was added 0.92 g of a sucrose fatty acid ester (manufactured by Mitsubishi-Kagaku Foods Corporation, trade name: S-370) as a surfactant and 0.92 g of a maleic anhydride-modified ethylene-propylene copolymer (manufactured by Mitsui Chemicals, Inc., trade name: HIWAX 1105A) as a hydrophobic polymeric dispersion agent, and then this was warmed up to 75 to 80° C. with a water bath at 85° C. at a stirring rate of 300 rpm to dissolve and disperse it before the stirring rate was increased up to 500 rpm to air cool it to an inner temperature of 61° C.

A nozzle (made by fluororesin tube with an inside diameter of 1 mm) with an inside diameter of 1 mm was attached to the tip of the tube of the tube pump (MASTERFLEX L/S series) previously prepared, the nozzle is fixed to a opening at the six openings of the separable cover, and the above-mentioned aqueous solution of the water-soluble ethylenically unsaturated monomer was added to the above-mentioned heptane stirring at 500 rpm (while keeping in mind that an aqueous monomer solution is not contacted with the wall surface) in a pump flow rate of 21 ml/min (observed separately). (The addition of the total amount of the above-mentioned aqueous monomer solution required about 600 seconds.) From Cross-sectional area A=$\pi/4\times0.1\times0.1$=$7.85\times10^{-3}$ [$m^2$]=$7.85\times10^{-7}$ [$m^2$], and Linear flow rate F=21 [ml/min]/($7.85\times10^{-3}$ [$m^2$])$\times$0.01 [m/cm]=26.8 [m/min], Addition rate V=F$\times$100 [cm/m]$\times$A/207 [ml]=0.10 [$min^{-1}$] was calculated at this time. The aqueous monomer solution was dispersed with keeping 500 rpm after an addition of the aqueous monomer solution. The atmosphere in the system was well substituted with nitrogen while maintaining the inner temperature of the round-bottom flask at 40° C., and a radical polymerization reaction was performed by warming for 1 hour with a hot water bath at 70° C.

Subsequently, according to the same manner as that of Example 1 Hereinafter, the process (D) of Example 1 or subsequent ones was performed similarly, and the water-absorbent resin 235 g of the form which spherical particles aggregated was obtained. This water-absorbent resin had a median particle size of 369 μm, and a water content of 5.3%.

Example 3

The addition rate of the aqueous monomer solution in Example 2 was changed to make Example 3.

Specifically, into a 500 mL Erlenmeyer flask, 92.0 g of 80% by mass of acrylic acid was charged and neutralized by adding dropwise 102.2 g of 30% by mass sodium hydroxide under stirring while cooling the flask from the outside. To this were added 0.11 g of potassium persulfate, 8.3 mg of ethylene glycol diglycidyl ether and 43.6 g of ion-exchange water to prepare an aqueous solution of a water-soluble ethylenically unsaturated monomer.

In a 2 L volumetric six-necked round-bottom flask equipped with a stirrer having a two-stage pitched blade paddle impellers of 50 mm in diameter, a thermometer, a reflux condenser and a nitrogen gas introducing tube, 334 g of n-heptane was weighted as a petroleum hydrocarbon dispersion medium. To the round-bottom flask were added 0.46 g of an oxidized ethylene-propylene copolymer (manufactured by Mitsui Chemicals, Inc., trade name: HIWAX 4052E) and 0.46 g of a maleic anhydride-modified ethylene-propylene copolymer (manufactured by Mitsui Chemicals, Inc., trade name: HIWAX 1105A) substituted for 0.92 g of a maleic anhydride-modified ethylene-propylene copolymer (manufactured by Mitsui Chemicals, Inc., trade name: HIWAX 1105A) as a hydrophobic polymeric dispersion agent, and then this was warmed up to 83 to 86° C. with a water bath at 90° C. at a stirring rate of 300 rpm to dissolve and disperse it before air cooling to an inner temperature of 61° C.

A nozzle (made by fluororesin tube with an inside diameter of 1 mm) with an inside diameter of 1 mm was attached to the tip of the tube of the tube pump (MASTERFLEX L/S series) previously prepared, the nozzle is fixed to a opening at the six openings of the separable cover, and the above-mentioned aqueous solution of the water-soluble ethylenically unsaturated monomer was added to the above-mentioned heptane stirring at 300 rpm (while keeping in mind that an aqueous monomer solution is not contacted with the wall surface) in a pump flow rate of 13 ml/min (observed separately). (The addition of the total amount of the above-mentioned aqueous monomer solution required about 960 seconds.) Cross-sectional area A=$\pi/4\times0.1\times0.1$=$7.85\times10^{-3}$ [$m^2$]=$7.85\times10^{-7}$ [$m^2$], Linear flow rate F=13 [ml/min]/($7.85\times10^{-3}$ [$m^2$])$\times$0.01 [m/cm]=16.6 [m/min], Addition rate V=F[m/min]$\times$100 [cm/m]$\times$A[$cm^2$]/207 [ml]=0.063 [$min^{-1}$] was calculated at this time. After adding the aqueous monomer solution, it was agitated at an inner temperature of 40° C. for 10 minutes and primarily dispersed. (step (A))

Next, a solution separately prepared by warming 0.92 g of a sucrose fatty acid ester (manufactured by Mitsubishi-Kagaku Foods Corporation, trade name: S-370) as a surfactant to dissolve it in 8.28 g of n-heptane by warming at 60° C. or higher was added to the round-bottom flask through a funnel and then a stirring rate was increased to 500 rpm to secondly disperse the aqueous monomer solution. (step (B))

Next, the atmosphere in the system was well substituted with nitrogen while maintaining the inner temperature of the round-bottom flask containing the dispersion at 40° C., and a radical polymerization reaction was performed by warming for 1 hour with a hot water bath at 70° C. (step (C))

After completion of the first stage polymerization, the stirring rate was increased to 1,000 rpm and the inner temperature was cooled to near 25° C. to precipitate at least a part of the surfactant. (step (D))

Separately, to a 500 mL Erlenmeyer flask, 128.8 g of 80 mass % acrylic acid was added and neutralized by adding dropwise 142.9 g of 30 mass % sodium hydroxide under stirring while cooling the flask from the outside. To this were added 0.15 g of potassium persulfate, 11.6 mg of ethylene glycol diglycidyl ether and 16.7 g of distilled water to prepare an aqueous monomer solution in the second stage polymerization. Next, the aqueous monomer solution was added to the cooled polymerization liquid (after step (D)) by full opening the cock part of a dropping funnel having an inside diameter of 4.5 mm at an addition opening, stirred to mix for some time, and absorbed into a polymerization gel at the first stage. The time period required to add an aqueous monomer solution at this time is 55 seconds, and by converting the aqueous monomer solution of 288.6 g by the specific gravity of 1.17 g/ml, and dividing the volume of 246.7 ml by 55 seconds to obtain Mean volume flow rate of 4.49 ml/sec at the pouring time, and from Cross-sectional area A=$\pi/4\times0.45$ [cm]$\times$0.45 [cm]=0.159 [$cm^2$]=$1.59\times10^{-5}$ [$m^2$], and Linear flow rate F=4.49 [ml/sec]/0.159 [$cm^2$]$\times$60 [sec/min]$\times$0.01 [m/cm]=16.84 [m/min], Addition rate V=F[m/min]$\times$100 [cm/m]$\times$A[$cm^2$]/246.7 [ml]=1.09 [$min^{-1}$] was calculated at this time. (step (E))

Next, the atmosphere in the system was well substituted with nitrogen while maintaining the inner temperature of the round-bottom flask containing the above dispersion liquid near room temperature, and a radical polymerization reaction was performed by warming for 1 hour with a hot water bath at 70° C. (step (F))

After the polymerization reaction in the second stage, the reaction suspension was heated using an oil bath at 120° C. and about 260 g of water was removed off from the system by azeotropic distillation while refluxing heptane in the flask to obtain a dehydrated polymer dispersed in heptane. To the resultant heptane dispersed dehydrated polymer, 8.2 g of a 2% aqueous solution of ethylene glycol diglycidyl ether as a post-crosslinking agent was added and the post-crosslinking reaction was performed at 83° C. for 2 hours.

Then, heating is performed using an oil bath at 120° C., n-heptane and water were removed off from the system by distillation, followed by drying under a nitrogen gas flow to obtain 236 g of a water-absorbent resin having in a form of aggregated spherical particles by passing through a sieve of 850 μm. This water-absorbent resin had a median particle size of 336 μm, and a water content of 5.1%.

Example 4

The addition rate of the aqueous monomer solution in Example 3 was changed to make Example 4.

In the rate of the aqueous monomer solution of the first stage polymerization with the tube pump in Example 3, the pump flow rate of 13 ml/min was substituted with 42 ml/min (observed separately). (The addition of the total amount of the above-mentioned aqueous monomer solution required about 300 seconds.) From Cross-sectional area $A=\pi/4 \times 0.1 \times 0.1 = 7.85 \times 10^{-3}$ [m$^2$]=$7.85 \times 10^{-7}$ [m$^2$], and Linear flow rate $F=42$ [ml/min]/($7.85 \times 10^{-3}$ [m$^2$])×0.01 [m/cm]=53.50 [m/min], Addition rate $V=F$[m/min]×100 [cm/m]×A[cm$^2$]/207 [ml]=0.20 [min$^{-1}$] was calculated at this time. After adding the aqueous monomer solution, it was agitated at an inner temperature of 40° C. for 10 minutes and primarily dispersed. (step (A))

Subsequently, according to the same manner as in Example 3, 235 g of a water-absorbent resin having in a form of aggregated spherical particles was obtained by passing through a sieve of 850 μm. This water-absorbent resin had a median particle size of 373 μm, and a water content of 5.3%.

Comparative Example 4

The addition rate of the aqueous monomer solution in Example 1 was increased to 0.30 [min$^{-1}$] or more as Comparative Example 4.

The aqueous monomer solution of the first stage polymerization was added by full opening the cock part of a dropping funnel having an inside diameter of 4.5 mm at an addition opening, substituted for the tube pump in Example 1. The time period required to add an aqueous monomer solution at this time is 48 seconds, and by converting the aqueous monomer solution of 238 g by the specific gravity of 1.15 g/ml, and dividing the volume of 207 ml by 48 seconds to obtain Mean volume flow rate of 4.31 ml/sec at the pouring time, Cross-sectional area $A=\pi/4 \times 0.45$ [cm]×0.45 [cm]=0.159 [cm$^2$]=$1.59 \times 10^{-5}$ [m$^2$], Linear flow rate $F=4.31$ [ml/sec]/0.159 [cm$^2$]×60 [sec/min]×0.01 [m/cm]=16.26 [m/min], and Addition rate $V=F$[m/min]×100 [cm/m]×A[cm$^2$]/207 [ml]=1.24 [min$^{-1}$] were calculated.

Subsequently, according to the same manner as in Example 1, 237 g of a water-absorbent resin having in a form of aggregated spherical particles was obtained by passing through a sieve of 850 μm.

This water-absorbent resin had a median particle size of 360 μm, and a water content of 5.4%.

Comparative Example 5

The addition rate of the aqueous monomer solution in Example 1 was increased to 0.30 [min$^{-1}$] or more to make Comparative Example 5.

The aqueous monomer solution of the first stage polymerization was added at a tube pump flow rate of 105 ml/min (observed separately) substituted for the tube pump of 21 ml/min in Example 1. (The addition of the total amount of the above-mentioned aqueous monomer solution required about 120 seconds.) From Cross-sectional area $A=\pi/4 \times 0.1 \times 0.1 = 7.85 \times 10^{-3}$ [m$^2$]=$7.85 \times 10^{-7}$ [m$^2$], and Linear flow rate $F=105$ [ml/min]/($7.85 \times 10^{-3}$ [m$^2$])×0.01 [m/cm]=133.8 [m/min], Addition rate $V=F$[m/min]×100 [cm/m]×A[cm$^2$]/207 [ml]=0.51 [min$^{-1}$] was calculated at this time. After adding the aqueous monomer solution, it was agitated at an inner temperature of 40° C. for 10 minutes and primarily dispersed. (step (A))

Subsequently, according to the same manner as in Example 1, 237 g of a water-absorbent resin having in a form of aggregated spherical particles was obtained by passing through a sieve of 850 μm. This water-absorbent resin had a median particle size of 353 μm, and a water content of 5.5%.

Example 5

Two sets of the tube pump for adding the aqueous monomer solution of the first stage polymerization in Example 2 were arranged, and this experiment added simultaneously was made into Example 5.

Two sets of the same type of tube pumps and nozzles having 1 mm in diameter of Example 2 were prepared respectively, and each nozzle was arranged in the approximately diagonal position for the separable cover to add 238 g of the aqueous monomer solution of the first stage polymerization simultaneously from two positions at 21 ml/min. The aqueous monomer solution was added at the rate of $V=0.10$ [min$^{-1}$] from each of the nozzles, and the time period required to add the aqueous monomer solution of the first stage polymerization was about 300 seconds which was half of that of Example 2. After adding the aqueous monomer solution, it was agitated at an inner temperature of 40° C. for 10 minutes and primarily dispersed. (step (A))

Subsequently, according to the same manner as in Example 2, 238 g of a water-absorbent resin having in a form of aggregated spherical particles was obtained by passing through a sieve of 850 μm. This water-absorbent resin had a median particle size of 350 μm, and a water content of 6.1%.

Example 6

Three sets of the tube pump for adding the aqueous monomer solution of the first stage polymerization in Example 2 were arranged, and this experiment added simultaneously was made into Example 6.

Three sets of the same type of tube pumps and nozzles having 1 mm in diameter of Example 4 were prepared respectively, and each nozzle was arranged in a position apart at an about 120° interval from the separable cover to add 238 g of the aqueous monomer solution of the first stage polymerization simultaneously from three positions at 21 ml/min. The aqueous monomer solution was added at the rate of $V=0.10$ [min$^{-1}$] from each of the nozzles, and the time period required to add the aqueous monomer solution of the first stage polymerization was about 200 seconds which was one third of that of Example 2. After adding the aqueous monomer solution, it was agitated at an inner temperature of 40° C. for 10 minutes and primarily dispersed. (step (A))

Subsequently, according to the same manner as in Example 2, 236 g of a water-absorbent resin having in a form of aggregated spherical particles was obtained by passing through a sieve of 850 μm. This water-absorbent resin had a median particle size of 367 μm, and a water content of 5.1%.

Each of Examples 1-6, and Comparative Examples 1-5 was carried out three times. For each of the resultant water-absorbent resins, an amount of the remaining dispersion medium was measured by using a measuring method of measuring an amount of a remaining dispersion medium, Mean±Standard deviation for them are shown in Table 1.

TABLE 1

| Samples | Dispersion at first stage | Aqueous monomer solution at first stage Devices | Aqueous monomer solution at first stage Addition rate V[min⁻¹] | Stirring rate [rpm] Step (A) | Stirring rate [rpm] Steps (B)-(C) | Aqueous monomer solution at second stage V[min⁻¹] | Amount of remaining dispersion medium [ppm] Mean ± Standard deviation (n = 3) |
|---|---|---|---|---|---|---|---|
| Comparative Example 1 | 2 steps | Funnel | 5.00 | 300 | 500 | 1.09 | 357 ± 8.0 |
| Comparative Example 2 | 2 steps | Funnel | 5.00 | 300 | 500 | 1.09 | 104 ± 6.0 |
| Example 1 | 2 steps | TP | 0.10 | 300 | 500 | 0.10 | 78 ± 3.6** |
| Example 2 | 2 steps | TP | 0.10 | 300 | 500 | 0.10 | 52 ± 3.0** |
| Example 3 | 2 steps | TP | 0.063 | 300 | 500 | 1.09 | 50 ± 3.1** |
| Example 4 | 2 steps | TP | 0.20 | 300 | 500 | 1.09 | 72 ± 4.0** |
| Comparative Example 3 | 1 step | TP | 0.10 | None | 500 | 0.10 | 2332 ± 67.5 |
| Comparative Example 4 | 2 steps | Dropping funnel | 1.24 | 300 | 500 | 0.10 | 244 ± 6.1 |
| Comparative Example 5 | 2 stages | TP | 0.51 | 300 | 500 | 0.10 | 163 ± 5.3 |
| Example 5 | 2 stages | TP ×2 | 0.10 | 300 | 500 | 0.10 | 54 ± 2.1** |
| Example 6 | 2 stages | TP ×3 | 0.10 | 300 | 500 | 0.10 | 60 ± 4.2** |

TP Abbreviated expression of tube pump
**p < 0.01 (vs. each of Comparative Examples 1 to 5)

From Table 1, controlling the addition rate in the polymerization system for the aqueous monomer solution of the first stage polymerization to an addition rate of 0.30 [min⁻¹] or less, could have accomplished an amount of the remaining dispersion medium of 80 ppm or less, to which it has been considered in the conventional method that it was difficult to reduce the amount of the remaining dispersion medium.

Moreover, from Examples 5 and 6, when an aqueous solution of the water-soluble ethylenically unsaturated monomer was also added by using two or three pouring nozzles having an addition rate V of 0.30 [min⁻¹] or less in the above-mentioned step (A), the same result as Example using one pouring nozzle was obtained, and thereby an influence of the number of nozzles has not been observed.

INDUSTRIAL APPLICABILITY

The present invention provides a method for producing a water-absorbent resin, wherein an amount of a remaining petroleum hydrocarbon dispersion medium used in a reversed phase suspension polymerization, which is contained in the water-absorbent resin and an odor originated form the petroleum hydrocarbon dispersion medium is further reduced, and a water-absorbent resin obtained by the method.

The invention claimed is:

1. A method for producing a water-absorbent resin by a multi-stage reversed-phase suspension polymerization to polymerize a water-soluble ethylenically unsaturated monomer, wherein the first stage polymerization comprising at least the following steps:
(A) performing a primary dispersion in the absence of surfactants by stirring to mix an aqueous solution of a water-soluble ethylenically unsaturated monomer containing a water-soluble radical polymerization initiator in a petroleum hydrocarbon dispersion medium in which a hydrophobic polymeric dispersion agent is dispersed or dissolved;
(B) performing a secondary dispersion by adding a surfactant to the resultant dispersion liquid; and
(C) performing a radical polymerization to obtain water-absorbent resin particles in a hydrous gel state which disperse in the petroleum hydrocarbon dispersion medium; and
the second stage polymerization comprising at least the following steps:
(D) precipitating at least a part of the surfactant;
(E) stirring to mix the aqueous solution of the water-soluble ethylenically unsaturated monomer of the second stage polymerization containing a water-soluble radical polymerization initiator therein to be absorbed and aggregated in the polymerized gel at the first stage; and
(F) performing a radical polymerization again;
wherein the aqueous solution of the water-soluble ethylenically unsaturated monomer is added in step (A) to the petroleum hydrocarbon dispersion medium at an addition rate V of 0.30 [min⁻¹] or less defined by the following Equation (I):

$$V = F \times A / T$$

wherein V: Addition rate [min⁻¹], F: Average linear flow rate from nozzle [m/min], A: Cross-sectional area of nozzle [m²], and T: Total amount [m³] of aqueous monomer solution added to a polymerization reaction tank.

2. The method according to claim 1, wherein a post-crosslinking is performed by adding a post-crosslinking agent after completion of the multi-stage reversed-phase suspension polymerization comprising steps (A) to (F).

3. The method according to claim 1, wherein a weight ratio of the amount of water-soluble ethylenically unsaturated monomers used in the second stage polymerization to the amount of water-soluble ethylenically unsaturated monomers used in the first stage polymerization, is between 1.0 and 2.0.

4. The method for producing a water-absorbent resin according to claim 1, wherein the surfactant is at least one kind selected from the group consisting of polyglyceryl fatty acid ester, sucrose fatty acid ester, and sorbitan fatty acid ester.

5. The method for producing a water-absorbent resin according to claim 1, wherein the addition rate V from the pouring nozzle for the aqueous solution of the water-soluble ethylenically unsaturated monomer of the first stage polymerization in step (A), is within a range of 0.05 to 0.30 [$min^{-1}$].

6. The method according to claim 1, wherein two or more of pouring nozzles having an addition rate V of 0.3[$min^{-1}$] or less for the aqueous solution of the water-soluble ethylenically unsaturated monomer in the first stage polymerization, are arranged in a polymerization reaction tank for performing step (A) to provide the water-soluble ethylenically unsaturated monomer.

7. The method for producing a water-absorbent resin according to claim 1, wherein the hydrophobic polymeric dispersion agent is at least one kind selected from the group consisting of maleic anhydride-modified polyethylene, maleic anhydride-modified polypropylene, maleic anhydride-modified ethylene-propylene copolymer, a maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, and an oxidized ethylene-propylene copolymer.

8. The method for producing a water-absorbent resin according to claim 1, wherein the water-soluble ethylenically unsaturated monomer is at least one kind selected from the group consisting of acrylic acid and its salt, methacrylic acid and its salt, and acrylamide.

9. The method according to claim 1, wherein the petroleum hydrocarbon dispersion medium is at least one kind selected from the group consisting of an aliphatic hydrocarbon and an alicyclic hydrocarbon, having a carbon number of 6 to 8.

10. The method according to claim 2, wherein a weight ratio of the amount of water-soluble ethylenically unsaturated monomers used in the second stage polymerization to the amount of water-soluble ethylenically unsaturated monomers used in the first stage polymerization, is between 1.0 and 2.0.

11. The method for producing a water-absorbent resin according to claim 2, wherein the surfactant is at least one kind selected from the group consisting of polyglyceryl fatty acid ester, sucrose fatty acid ester, and sorbitan fatty acid ester.

12. The method for producing a water-absorbent resin according to claim 3, wherein the surfactant is at least one kind selected from the group consisting of polyglyceryl fatty acid ester, sucrose fatty acid ester, and sorbitan fatty acid ester.

13. The method for producing a water-absorbent resin according to claim 2, wherein the addition rate V from the pouring nozzle for the aqueous solution of the water-soluble ethylenically unsaturated monomer of the first stage polymerization in step (A), is within a range of 0.05 to 0.30 [$min^{-1}$].

14. The method for producing a water-absorbent resin according to claim 3, wherein the addition rate V from the pouring nozzle for the aqueous solution of the water-soluble ethylenically unsaturated monomer of the first stage polymerization in step (A), is within a range of 0.05 to 0.30 [$min^{-1}$].

15. The method for producing a water-absorbent resin according to claim 4, wherein the addition rate V from the pouring nozzle for the aqueous solution of the water-soluble ethylenically unsaturated monomer of the first stage polymerization in step (A), is within a range of 0.05 to 0.30 [$min^{-1}$].

16. The method for producing a water-absorbent resin according to claim 2, wherein the hydrophobic polymeric dispersion agent is at least one kind selected from the group consisting of maleic anhydride-modified polyethylene, maleic anhydride-modified polypropylene, maleic anhydride-modified ethylene-propylene copolymer, a maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, and an oxidized ethylene-propylene copolymer.

17. The method for producing a water-absorbent resin according to claim 3, wherein the hydrophobic polymeric dispersion agent is at least one kind selected from the group consisting of maleic anhydride-modified polyethylene, maleic anhydride-modified polypropylene, maleic anhydride-modified ethylene-propylene copolymer, a maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, and an oxidized ethylene-propylene copolymer.

18. The method for producing a water-absorbent resin according to claim 4, wherein the hydrophobic polymeric dispersion agent is at least one kind selected from the group consisting of maleic anhydride-modified polyethylene, maleic anhydride-modified polypropylene, maleic anhydride-modified ethylene-propylene copolymer, a maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, and an oxidized ethylene-propylene copolymer.

19. The method for producing a water-absorbent resin according to claim 5, wherein the hydrophobic polymeric dispersion agent is at least one kind selected from the group consisting of maleic anhydride-modified polyethylene, maleic anhydride-modified polypropylene, maleic anhydride-modified ethylene-propylene copolymer, a maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, and an oxidized ethylene-propylene copolymer.

* * * * *